(12) United States Patent
Wei et al.

(10) Patent No.: US 7,642,338 B2
(45) Date of Patent: Jan. 5, 2010

(54) TACROLIMUS STANDARD AND METHODS OF USING SAME

(75) Inventors: Tie Q. Wei, Bear, DE (US); David R. Hudson, Rising Sun, MD (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 123 days.

(21) Appl. No.: 11/455,956

(22) Filed: Jun. 20, 2006

(65) Prior Publication Data

US 2007/0292891 A1 Dec. 20, 2007

(51) Int. Cl.
*A61K 38/12* (2006.01)
*G01N 33/566* (2006.01)
*A61B 5/00* (2006.01)

(52) U.S. Cl. .................. 530/317; 436/501; 600/300
(58) Field of Classification Search .................. None
See application file for complete search history.

(56) References Cited

U.S. PATENT DOCUMENTS

| | | | |
|---|---|---|---|
| 3,817,837 A | | 6/1974 | Rubenstein et al. |
| 5,196,437 A | | 3/1993 | Starzl et al. |
| 5,260,301 A | | 11/1993 | Nakanishi et al. |
| 5,635,406 A | * | 6/1997 | Grenier et al. ............. 436/536 |
| 5,665,727 A | | 9/1997 | Grassberger et al. |
| 6,121,257 A | * | 9/2000 | Kawai et al. ................ 514/183 |
| 6,410,340 B1 | | 6/2002 | Soldin |
| 7,078,495 B1 | | 7/2006 | Kasper et al. |
| 2005/0112778 A1 | * | 5/2005 | Wang et al. .................. 436/501 |
| 2007/0087396 A1 | | 4/2007 | Konrath et al. |

FOREIGN PATENT DOCUMENTS

WO WO/01/09190 A2 2/2001

OTHER PUBLICATIONS

Burdnick, 2003, Medical Device Link, pp. 1-7.*
Retrieved from] http://www.biopharmlaboratories.com/BioPharm_Laboratories/BSA.html, 2009, 4 page [Retrived on Jan. 30, 2009].*
Schottelius, D. D., Homogeneous Immunoassay System (EMIT) . . . , Antiepileptic Drugs: Quantative Analysis and Interpretation, Raven Press, New York, 1978.
Wallemacq, et al., FK506 (Tacrolimus), a Novel Immunosuppressant in Organ Transplantation: . . . , Clinical Chemistry, (1993), vol. 39, No. 11, pp. 2219-2228.

* cited by examiner

*Primary Examiner*—Andrew D Kosar
*Assistant Examiner*—Satyanarayana R Gudibande
(74) *Attorney, Agent, or Firm*—Theodore J. Leitereg; Robert N. Carpenter

(57) ABSTRACT

A composition and kit useful as a tacrolimus standard solution for immunoassays, and methods for making and using same. The composition and kits include a known amount of tacrolimus or a derivative thereof, and a non-specific protein capable of forming a complex with the tacrolimus or derivative thereof. The standard solution may be used to generate calibration curves for an immunoassay or to check the precision of an analytical instrument.

12 Claims, No Drawings

TACROLIMUS STANDARD AND METHODS OF USING SAME

FIELD OF THE INVENTION

The present invention generally relates to tacrolimus standards. More particularly, the present invention relates to tacrolimus standards which utilize a protein non-specific for tacrolimus, and to methods of making and using such standards.

BACKGROUND OF THE INVENTION

Tacrolimus (also known as FK506) is a neutral macrolide isolated from the fungus *Streptomyces tsukubaenis*. Tacrolimus has been used clinically as an immunosuppressant in organ transplantation and for treating autoimmune diseases. See Wallemacq et al., "*FK 506 (Tacrolimus), a Novel Immunosuppressant in Organ Transplantation: Clinical, Biomedical, and Analytical Aspects*," Clinical Chemistry, 39/11, 2219-2228 (1993). As with many therapeutic drugs, it is desirable to be able to monitor the blood concentrations of tacrolimus quantitatively to ensure proper efficacy of the drug and to protect against possible toxicity during treatment.

A variety of measuring methods have been developed to monitor the blood concentrations of tacrolimus. Many of these methods require the use of a calibration curve for a chemical analyzer by using multiple calibration solutions or calibrators which have been carefully prepared with known, predetermined concentrations of tacrolimus. These calibration or standard solutions may be assayed one or more times and the mean resulting reaction signals are plotted versus their respective known tacrolimus concentrations. A continuous calibration curve may be produced using any of several mathematical techniques chosen to produce an accurate replication of the relationship between a reaction signal and the tacrolimus concentration. For greatest accuracy, calibration curves are established at regular intervals, to compensate for reagent particulars, and on individual analyzers, to compensate for equipment performance.

Several challenges have arisen in the preparation of tacrolimus calibrating and standard compositions. For example, some standard solutions for tacrolimus have are unstable and subject to rapid degradation, leading to inaccurate test results. Furthermore, tacrolimus is insoluble in water, and some standard solutions have included organic solvents that may leave residues or otherwise interfere with the operation or precision of test equipment such as automated analyzers.

Accordingly, there continues to be a need for improved tacrolimus standard compositions.

SUMMARY OF THE INVENTION

The composition of the present invention provides an improved, stable standard for tacrolimus.

In one aspect of the invention, a composition suitable for use as a standard in an assay includes a solution having a known amount of tacrolimus or a derivative thereof, and a protein non-specific for tacrolimus and capable of forming a soluble complex with the tacrolimus or the derivative thereof, the protein being essentially fatty acid free.

In another aspect of the invention, a composition suitable for use as a standard in an assay includes a solution having a known amount of tacrolimus or a derivative thereof, and a protein non-specific for tacrolimus and capable of forming a soluble complex with the tacrolimus or the derivative thereof, the solution being essentially free of organic solvents and proteins specific for tacrolimus or a derivative thereof.

In another aspect of the invention, a kit suitable for use in a diagnostic assay includes a first known amount of tacrolimus or a derivative thereof, and a protein capable of forming a water soluble complex with the tacrolimus or derivative thereof.

In another aspect of the invention, a method is provided for use in an assay for tacrolimus. The method includes providing a standard solution including a known amount of tacrolimus or a derivative thereof and a protein capable of forming a water soluble complex with the tacrolimus or derivative thereof, and performing an assay on the standard solution to determine a measurement corresponding to the known amount of tacrolimus or derivative thereof.

The foregoing paragraphs have been provided by way of general introduction, and are not intended to limit the scope of the following claims. The presently preferred embodiments, together with other aspects of the invention, will be best understood by reference to the following detailed description taken in conjunction with the accompanying drawings.

DETAILED DESCRIPTION OF EXEMPLARY EMBODIMENTS OF THE INVENTION

The present invention is directed generally to compositions and kits useful for assays for tacrolimus, and to methods of making and using the compositions and kits. The compositions of the present invention include a known amount of tacrolimus or a derivative thereof, and a sufficient amount of a protein non-specific for tacrolimus which is capable of forming a complex with the tacrolimus or the derivative thereof.

Tacrolimus has the formula:

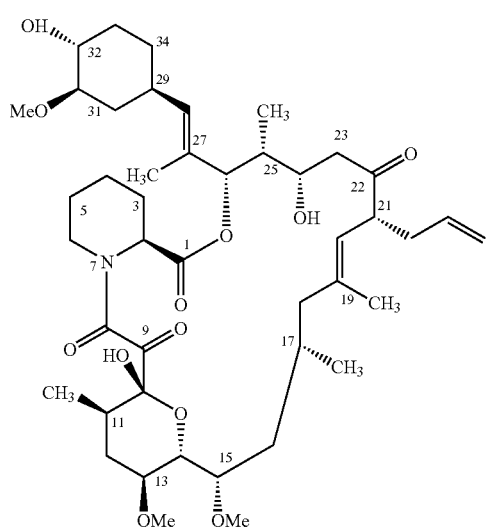

As used herein, a "derivative" of tacrolimus means a compound which generally retains the basic skeleton and/or properties of tacrolimus, but includes one or more substitutions. In many instances, these derivatives are themselves useful as reagents in an assay for tacrolimus. For example, a tacrolimus analogue labeled at the carbon 22 with a streptavidinylated enzyme is a known derivative useful in the EMIT® immunoassay for tacrolimus sold by Dade Behring, Inc., having a principal office in Deerfield, Ill.

Other examples of known derivatives include those disclosed in Ser. No. 10/719,868, filed on Nov. 21, 2003, entitled "Method and Composition Useful For Determining FK-506," which describes ester and carbamate derivatives at C-32 and/or C-24. Another example are the C-22 oxime derivatives disclosed in Ser. No. 09/368,010, filed on Aug. 3, 1999, entitled "Monoclonal Antibodies To Tacrolimus And Immunoassay Methods For Tacrolimus." Other examples of suitable known derivatives are disclosed in U.S. Pat. Nos. 5,260,301, 5,196,437, and 5,665,727.

The non-specific binding proteins useful in the present invention are any of those that are capable of forming a complex with tacrolimus or a derivative thereof, are stable enough to allow for dissolution of the tacrolimus in solution, and do not specifically bind to tacrolimus.

In one embodiment of the invention, the non-specific protein is a hydrophilic protein with hydrophobic cavities on the molecular surface. The tacrolimus is complexed to the hydrophobic cavities of the non-specific protein through non-covalent bonding, such as through hydrogen bonding. Suitable proteins include albumin and $\alpha_1$-acid glycoprotein. In one embodiment of the invention, the albumin is bovine serum albumin.

In a preferred embodiment of the invention, the non-specific binding protein is treated to remove fatty acids from their hydrophobic cavities. The absence of the fatty acids allows for a more stable complex between the tacrolimus and the hydrophobic cavity. In especially preferred embodiments of the invention, the protein is essentially fatty acid free bovine serum albumin or $\alpha_1$-acid glycoprotein. Essentially fatty acid free bovine serum albumin is commercially available, for example, from Sigma-Aldrich-Fluka of Saint Louis, Mo.

As used herein, "essentially fatty acid free" refers to proteins that are free of fatty acids as well proteins that are essentially fatty acid free but may have small residual amounts of fatty acid that do not substantially interfere with the binding of tacrolimus to the protein. Generally, proteins may be essentially fatty acid free if they are at least 95% fatty acid free, more preferably, at least 97% fatty acid free, and even more preferably, at least 99% fatty acid free. Fatty acids may be removed from non-specific protein according to methods known in the art. One such method includes precipitation of the fatty acids with cold alcohols.

The non-specific binding protein should be present in an amount sufficient to allow for tacrolimus or derivative thereof to dissolve in solution. Typically, the ratio of protein to tacrolimus will range from 25,000:1 to 1,000:1 on a weight basis. In some embodiments, the protein to tacrolimus weight ratio will be at least about 2,000:1, or at least about 5,000:1, or at least about 10,000:1.

In one embodiment of the invention, the composition includes an aqueous solution. Typically, tacrolimus or the derivative thereof will be present in an amount of about 0.1 to about 10.0 mg per 100 ml of water. The protein typically will be present in an amount of about 1 g to about 25 g per 100 ml water.

In another embodiment of the invention, the composition is free or substantially free of organic solvents. In a preferred embodiment, the composition is free or substantially free of alkanol solvents, such as methanol, ethanol, propanol, etc. The elimination of organic solvents from the composition provides the benefit that less organic residue is left on any equipment such as analyzer using the composition, thereby making it easier to maintain the precision of the equipment over time.

In another embodiment of the invention, the compositions may be essentially free of proteins that bind specifically to tacrolimus or a derivative thereof. Elimination of specific binding proteins reduces cost and results in a solution having fewer interfering compounds.

In other embodiments of the invention, the composition may include other components or additives. In one particular embodiment of the invention, an emulsifier is added to the solution. The emulsifier is particularly useful in an aqueous solution to assist in dissolution of the tacrolimus or derivative thereof. Suitable emulsifiers include non-ionic emulsifiers such polyoxylated caster oils. One such emulsifier is sold by BASF under the registered trademark "Cremophor® EL" and is preferably used in composition in the range of 0.01% to 0.5% by weight. Other suitable emulsifiers include, without limitation, saponin, sodium dodecyl sulfate, and lithium dodecyl sulfate.

In another embodiment of the invention, a composition useful for a tacrolimus standard includes a known amount of tacrolimus or a derivative thereof and an emulsifier capable of solubilizing the tacrolimus or derivative in solution as described above.

In another embodiment of the invention, the composition may be stored as a stock solution for later dilution. In one embodiment, the stock solution is diluted with a hemolysate base. For example, the stock solutions may be diluted by about 1:10 to 1:1000, more typically 1:50 to about 1:500 prior to use. Typically, the hemolysate is made from whole blood preserved in EDTA and which has been exposed to repeated freeze and thaw cycles. In other embodiments, the hemolysate may be made from one or more blood components.

According to another aspect of the present invention, the compositions described above may be used in methods of detecting the presence or amount of tacrolimus in a sample. Suitable assay techniques include immunoassays techniques generally known in the art.

The compositions of the present invention include a known amount of tacrolimus. Accordingly, assays for tacrolimus may be performed on the compositions in order to establish a calibration curve for response of a particular technique. In one embodiment, multiple compositions having varying concentrations of tacrolimus or the derivative thereof may be assayed in order to provide multiple points for the establishment of a calibration curve.

In general, an assay technique according to the present invention includes the steps of:

(1) providing a sample suspected of containing tacrolimus;
(2) reacting the sample with:
  (a) an antibody against tacrolimus; and
  (b) optionally, with a tacrolimus analogue, wherein one of the antibody or the tacrolimus analog is labeled with a label producing a detectable signal; and
(3) observing or measuring one of:
  (a) a signal associated with tacrolimus bound to antibody;
  (b) a signal associated with tacrolimus unbound to antibody; or
  (c) total signal present to detect or determine the presence or concentration of tacrolimus in the sample.

Such assays are described as either homogeneous or heterogeneous. In a heterogeneous assay, the antibody bound to antigen is separated from antibody unbound to antigen. This separation can be done by a number of steps well known in the art, such as differential solubility, reactivity with another antibody, or other properties. Such assays are well known in the art and need not be described further in detail here. If either the signal associated with tacrolimus bound to antibody or the signal associated with tacrolimus unbound to antibody is to be detected or determined, a heterogeneous assay is performed. By contrast, in a homogeneous assay, the total signal present is detected or determined. In a homogeneous assay, the existence of an antigen-antibody complex modulates the signal so that the signal level changes without a requirement of separating antigen bound to antibody from antigen unbound to antibody.

An example of a suitable homogeneous immunoassay system is known as EMIT, as described in D. D. Schottelius, "Homogeneous Immunoassay System (EMIT) for Quantitation of Antiepileptic Drugs in Biological Fluids" in Antiepileptic Drugs: Quantitative Analysis and Interpretation (C. E. Pippenger et al., Raven Press, New York, 1978, Chapt 10, pp. 98-101) and further described in U.S. Pat. No. 3,817,837. An example of a heterogeneous assay is an affinity column mediated immunometric assay (ACMIA).

According to another aspect of the invention, kits are provided for use in an assay for tacrolimus. The kits include a known amount of tacrolimus or a derivative thereof, and a sufficient amount of a non-specific protein capable of forming a complex with the tacrolimus or a derivative thereof. In one embodiment, the protein is essentially fatty acid free. In another embodiment, the kit is essentially free of organic solvents and proteins that specifically bind to tacrolimus or a derivative thereof.

The tacrolimus and non-specific protein may be packaged together, or may be packaged separately. The components may be in solution, or in a preferred embodiment, may be lyophilized for adding shelf life to the components.

In one preferred embodiment of the kit, non-specific protein is present in an amount of about 1 g to about 25 g, and the tacrolimus is present in an amount of about 0.1 mg to about 10 mg.

The kit may also include other suitable materials, such distilled water, an emulsifier, an enzyme label, a hemolysate, or other components of the compositions discussed above. The kit may also contain written instructions for use of the tacrolimus and non-specific protein to carry out the methods described as described herein.

The kit may contain single known amount of tacrolimus or a derivative thereof, or it may contain multiple known amounts. For example, the kit may contain a first known amount of tacrolimus and a second known amount, where the second known amount is different than the first amount. Likewise, the kit may contain a third known amount, a fourth known amount, and so on, each known amount being different from the other known amounts. Performing an assay on each known amount allows for the determination of multiple data points for use in construction of a calibration curve.

EXAMPLE 1

Preparation of a Tacrolimus Standard Solution 14 grams of bovine serum albumin, fatty acid free, (from Sigma-Aldrich-Fluka) was mixed with 100 ml purified water to form a solution. As a control, a 50/50 wt % solution of methanol and water was prepared. To each solution, 1.00 mg of tacrolimus was added and allowed to stir at room temperature for 24 hours. 250 µL of Cremophor® EL, (CAS Number 61791-12-6) was added to each solution to act as an emulsifier. Each solution was then diluted 1:25 in water, and then further diluted 1:10, again in water, for a final dilution ratio of 1:250. Each sample was tested on the Dimension® RxL Max® integrated chemistry analyzer using an affinity column mediated immunometric assay. The analyzer was first calibrated using a tacrolimus master pool supplied by Bioresources of Fort Lauderdale, Fla. The bovine serum solution and the control solution yielded substantially equivalent results (6150 ng/mL and 5985 ng/mL, respectively).

EXAMPLE 2

Effect of Protein and Emulsifier on Tacrolimus Recovery

The testing procedure of Example 1 was repeated on the samples identified in Table 1 in order to study the effect of the protein and the emulsifier on tacrolimus recovery. Each of the samples were dissolved in 100 ml water, and then diluted with 1:500 with water. The results demonstrate that both the fatty acid free BSA and the emulsifier contribute to the recovery of tacrolimus.

TABLE 1

| Sample | Description | Tacrolimus Recovery |
|---|---|---|
| 1 | 10 mg Tacrolimus | 0% |
| 2 | 10 mg Tacrolimus<br>14 g FAF BSA | 35% |
| 3 | 10 mg Tacrolimus<br>250 µL Cremophor ® EL | 30% |
| 4 | 10 mg Tacrolimus<br>14 g FAF BSA<br>250 µL Cremophor ® EL | 60% |

EXAMPLE 3

Effect of Fatty Acid Removal from Protein on Tacrolimus Recovery

The testing procedure of Example 1 was repeated on the samples identified in Table 2 in order to study the effect of the removal of fatty acids from the protein on tacrolimus recovery. Each of the samples were dissolved in 100 ml water, and then diluted with 1:500 with water. The results demonstrate that rendering the BSA fatty acid free significantly increases the tacrolimus recovery.

TABLE 2

| Sample | Description | Tacrolimus Recovery |
|---|---|---|
| 5 | 10 mg Tacrolimus<br>6 g BSA (with fatty acids)<br>250 µL Cremophor ® EL | 32% |
| 6 | 10 mg Tacrolimus<br>6 g FAF BSA<br>250 µL Cremophor ® EL | 51% |

EXAMPLE 4

Comparison of Fatty Acid Free Bovine Serum Albumin Concentrations on Tacrolimus Recovery The testing procedure of Example 1 was repeated on the samples identified in Table 3 in order to study the effect of the concentration of the protein on tacrolimus recovery. Each of the samples were dissolved in 100 ml water, and then diluted with 1:500 with water. The results demonstrate that tacrolimus recovery is a function of BSA concentration.

TABLE 3

| Sample | Description | Tacrolimus Recovery |
|---|---|---|
| 7 | 10 mg Tacrolimus<br>6 g FAF BSA<br>250 µL Cremophor ® EL | 32% |
| 8 | 10 mg Tacrolimus<br>8 g FAF BSA<br>250 µL Cremophor ® EL | 42% |
| 9 | 10 mg Tacrolimus<br>11 g FAF BSA<br>250 µL Cremophor ® EL | 45% |
| 10 | 10 mg Tacrolimus<br>14 g FAF BSA<br>250 µL Cremophor ® EL | 54% |

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

The invention claimed is:

1. A method for use in determining a concentration of tacrolimus or derivative thereof in a sample, said method comprising: providing a standard solution including a known amount of tacrolimus or a derivative thereof and a non-specific protein capable of forming a water soluble complex with the tacrolimus or derivative thereof, the non-specific protein being at least 95% fatty acid free and the ratio of non-specific protein to tacrolimus being in the range of 25,000:1 to 1000:1 on a weight basis wherein the non-specific protein is albumin or $\alpha_1$-acid glycoprotein; and performing an assay on the standard solution and on the sample to determine a concentration of tacrolimus or derivative thereof in the sample.

2. The method of claim 1, wherein the standard solution further includes an emulsifier.

3. The method of claim 1, wherein the standard solution further includes a hemolysate.

4. The method of claim 1, wherein the solution comprises fatty acid free bovine serum albumin.

5. The method of claim 1, wherein standard solution is free of alkanol solvents.

6. The method of claim 1 wherein the ratio of non-specific protein to tacrolimus is at least 2,000:1 on a weight basis.

7. The method of claim 1 wherein the ratio of non-specific protein to tacrolimus is at least 5,000:1 on a weight basis.

8. The method of claim 1 wherein the ratio of non-specific protein to tacrolimus is at least 10,000:1 on a weight basis.

9. A method for use in determining a concentration of tacrolimus or derivative thereof in a sample, said method comprising: providing a standard solution including a known amount of tacrolimus or a derivative thereof and a non-specific protein capable of forming a water soluble complex with the tacrolimus or derivative thereof, the non-specific protein being at least 95% fatty acid free and the ratio of non-specific protein to tacrolimus being at least 2000:1 on a weight basis wherein the non-specific protein is albumin or $\alpha_1$-acid glycoprotein; and performing an assay on the standard solution and on the sample to determine a concentration of tacrolimus or derivative thereof in the sample.

10. The method of claim 9, wherein the standard solution further includes an emulsifier.

11. The method of claim 9, wherein the solution comprises fatty acid free bovine serum albumin.

12. The method of claim 9, wherein standard solution is free of alkanol solvents.

* * * * *